United States Patent
Sato et al.

(10) Patent No.: US 9,655,830 B2
(45) Date of Patent: May 23, 2017

(54) COSMETIC COMPOSITION

(75) Inventors: Minako Sato, Yokohama (JP); Takashi Teshigawara, Yokohama (JP); Kei Watanabe, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 735 days.

(21) Appl. No.: 13/519,348

(22) PCT Filed: Dec. 27, 2010

(86) PCT No.: PCT/JP2010/073571
§ 371 (c)(1),
(2), (4) Date: Feb. 13, 2013

(87) PCT Pub. No.: WO2011/081136
PCT Pub. Date: Jul. 7, 2011

(65) Prior Publication Data
US 2013/0150328 A1  Jun. 13, 2013

(30) Foreign Application Priority Data
Dec. 28, 2009  (JP) ................................. 2009-297165

(51) Int. Cl.
*A61Q 19/00* (2006.01)
*A61K 8/55* (2006.01)
*A61K 8/34* (2006.01)
*A61K 8/36* (2006.01)

(52) U.S. Cl.
CPC .............. *A61K 8/553* (2013.01); *A61K 8/342* (2013.01); *A61K 8/345* (2013.01); *A61K 8/361* (2013.01); *A61Q 19/00* (2013.01); *A61K 2800/262* (2013.01)

(58) Field of Classification Search
CPC ... A61K 8/14; A61K 8/42; A61K 8/44; A61K 8/553; A61K 8/606; A61Q 17/00; A61Q 19/00; A61Q 19/08
See application file for complete search history.

(56) References Cited

U.S. PATENT DOCUMENTS

| 7,001,604 B2* | 2/2006 | Albrecht et al. ............. 424/401 |
| 2005/0064025 A1* | 3/2005 | Litchenberger et al. ..... 424/450 |

FOREIGN PATENT DOCUMENTS

| JP | 60-146812 | * 8/1985 | ............ 424/401 |
| JP | 60146812 | * 8/1985 | ............ 424/401 |
| JP | 2007-314442 | 12/2007 | |
| JP | 2008-162932 | 7/2008 | |
| JP | 2009-013864 | 1/2009 | |
| JP | 5623076 | 11/2014 | |
| WO | 2009/013864 | 1/2009 | |

OTHER PUBLICATIONS

Yamada Shunji et al. Thickening/Gelling Agent Composition. JP60146812A, published 19850802. Translation.*
Database GNPD [Online] Mintel; Mar. 2009, "Facial Mask", XP-002738719, Database accession No. 1064936, total 7 pages.; Cited in EESR.
Database GNPD [Online] Mintel; Apr. 2009, "Skin Moisturizer II", XP-002738720, Database accession No. 1211162, total 4 pages.; Cited in EESR.
Extended European Search Report dated May 7, 2015 issued in the corresponding European patent application No. 10840992.1.

* cited by examiner

Primary Examiner — Audrea Buckley
(74) Attorney, Agent, or Firm — Rankin, Hill & Clark LLP

(57) ABSTRACT

To provide a transparent to translucent cosmetic composition which is highly stable, and can impart excellent actual feelings of effectiveness in use, such as a feeling of skin penetration, a feeling of non-stickiness, and a skin-softening effect after application thereof to the skin. A transparent to translucent cosmetic composition comprising: (a) a hydrogenated phospholipid, (b) one or more selected from among branched higher fatty acids and higher alcohols, and (c) a polyalcohol that acts as a good solvent and/or a poor solvent for component (a). Preferably, component (b) is isostearic acid and/or isostearyl alcohol. Preferably, the ratio of component (a)/component (b) is from 1/0.01 to 1/0.4 (by mass).

14 Claims, No Drawings

COSMETIC COMPOSITION

TECHNICAL FIELD

The present invention relates to a cosmetic composition. More precisely, the invention relates to a transparent to translucent cosmetic composition which is highly stable, and can impart excellent actual feelings of effectiveness in use, such as a feeling of skin absorption or skin penetration, a feeling of non-stickiness, and a skin-softening effect after application thereof to the skin.

BACKGROUND ART

A skin cosmetic composition such as typically lotion is desired to be able to impart excellent actual feelings of effectiveness in use, such as a feeling of skin absorption or skin penetration, a feeling of non-stickiness, and a skin-softening effect after application thereof to the skin. Incidentally, a phospholipid that is a main ingredient of lecithin is known as a constituent component of biomembrane, and has heretofore been used as a high safety naturally-derived surfactant. Furthermore, as being a biomembrane constituent component, the phospholipid has a good affinity to skin and is therefore specifically noted as a component having excellent actual feelings of effectiveness in use, and its practical use to cosmetic bases has been made (for example, see Patent Reference 1).

However, the incorporation of lecithin into a low-viscosity cosmetic composition such as lotion or the like, may cause a precipitation. Accordingly, for increasing the dispersibility thereof, lecithin is often used along with a nonionic surfactant (for example, see Patent Reference 2). A nonionic surfactant can enhance the stability of the system, but when incorporated too much, it tends to detract from the effects of actual feelings in use specific to lecithin.

Consequently, it is desired to develop a cosmetic composition excellent in stability not detracting from the actual feelings of effectiveness in use specific to lecithin.

As the prior art close to the present invention using lecithin, there are known a method comprising dissolving a phospholipid such as soybean lecithin or the like in a polyalcohol that acts as a good solvent, then adding thereto another polyalcohol that acts as a poor solvent to form a lamellar liquid crystal, and gradually and dropwise adding thereto water or an aqueous solution to prepare an aqueous dispersion of fine liposomes (see Patent Reference 3), and a solubilized transparent cosmetic composition containing a specific monoacyl-type phospholipid (see Patent Reference 4). However, these patent references do neither describe nor suggest an idea of obtaining a cosmetic composition which is excellent in stability not detracting from the actual feelings of effectiveness in use specific to lecithin and has a translucent to transparent appearance.

PRIOR ART REFERENCES

Patent References

Patent Reference 1: JP 62-93239A
Patent Reference 2: JP 3298867B
Patent Reference 2: JP 4-208216A
Patent Reference 3: JP 4-49214A

SUMMARY OF INVENTION

Problems that Invention is to Solve

The present invention has been made in consideration of the above-mentioned situation, and its object is to provide a transparent to translucent cosmetic composition which is highly stable, and can impart excellent actual feelings of effectiveness in use, such as a feeling of skin penetration, a feeling of non-stickiness, and a skin-softening effect after application thereof to the skin.

Means for Solving the Problems

In order to solve the above-mentioned problems, the present invention provides a transparent to translucent cosmetic composition comprising (a) a hydrogenated phospholipid, (b) one or more selected from among branched higher fatty acids and higher alcohols, and (c) a polyalcohol that acts as a good solvent and/or a poor solvent for component (a).

The invention also provides the above-mentioned cosmetic composition, in which component (b) is isostearic acid and/or isostearyl alcohol.

The invention also provides the above-mentioned cosmetic composition, in which the ratio of component (a)/component (b) is from 1/0.01 to 1/0.4 (by mass).

The invention also provides the above-mentioned cosmetic composition, in which the phosphatidylcholine content in component (a) is at least 60% by mass.

Advantageous Effects of Invention

According to the invention, there is provided a transparent to translucent cosmetic composition which is highly stable, and can impart excellent actual feelings of effectiveness in use, such as a feeling of skin penetration, a feeling of non-stickiness, and a skin-softening effect after application thereof to the skin.

MODE FOR CARRYING OUT INVENTION

The invention is described in detail hereinunder.

The hydrogenated phospholipid of component (a) includes those prepared by hydrogenating natural lecithin, such as soybean lecithin, egg yolk lecithin or the like, according to an ordinary method, as well as those prepared by hydrogenating phosphatidylcholine, phosphatidylethanolamine, and phosphatidylserine, etc. The hydrogenated phospholipid has a few unsaturated groups and its stability is therefore high; and when incorporated in a cosmetic composition, the stability to heat and oxidation becomes higher. In the invention, preferred is a soybean lecithin-derived, hydrogenated soybean phospholipid in view of the stability thereof.

As component (a), preferred is use of one having a phosphatidylcholine (PC) content of at least 60% by mass, from the viewpoint of the solubility thereof in solvent, etc., more preferably at least 75% by mass. When a hydrogenated phospholipid having a low PC content is used, its solubility in solvent is poor and preferred liquid crystal formation could not be attained. As the specific examples of the component (a), for example, commercial products thereof include COATSOME NC-21 (having a PC content of 90% by mass or more, by NOF Corporation), COATSOME NC-61 (having a PC content of 60% by mass or more, by NOF Corporation), NIKKOL Lecinol S-10E (having a PC content of from 75 to 85% by mass, by Nikko Chemicals Co., Ltd.), NIKKOL Lecinol S-10EX (having a PC content of 95% by mass or more, by Nikko Chemicals Co., Ltd.), BASIS LP-60HR (having a PC content of from 62 to 68% by mass, by Nisshin Oillio Group, Ltd.), etc. One or more are used as component (a).

The amount of component (a) is preferably from 0.001 to 3% by mass in the cosmetic composition of the invention, more preferably from 0.01 to 1% by mass, most preferably from 0.01 to 0.5% by mass. When the amount of component (a) is less than 0.001% by mass, then the actual feelings of effectiveness in use may tend to worsen; but on the other hand, when incorporated in an amount more than 3% by mass, the component may tend to precipitate to worsen the stability of the preparation.

Component (b) is one or more selected from among branched higher fatty acids and higher alcohols.

The branched higher fatty acids include saturated fatty acids having from 12 to 22 carbon atoms, such as isopalmitic acid, and isostearic acid. Above all, isostearic acid is preferred from the viewpoint of the stability, etc.

The branched higher alcohols include higher alcohols having from 12 to 28 carbon atoms. Above all, preferred is isostearyl alcohol from the viewpoint of the stability of the composition, etc.

In the cosmetic composition of the invention, preferably, component (b) is incorporated in a ratio, component (a)/component (b) of from 1/0.01 to 1/0.4 (by mass), more preferably from 1/0.05 to 1/0.3 (by mass). When the amount of component (b) is in the ratio as above, the stability of the system of the cosmetic composition can be enhanced more.

The polyalcohol for component (c) is a good solvent and/or a poor solvent for component (a). Exemplary polyalcohol acting as a good solvent include 1,3-butylene glycol, dipropylene glycol, and propylene glycol. Exemplary polyalcohol acting as a poor solvent include glycerin, polyethylene glycol 400, polyoxyethylene (hereinafter designated as "POE") methylglucoside, polyoxypropylene (hereinafter designated as "POP") methylglucoside, sorbitol, POE (14) POP (7) dimethyl ether, and POE (17) POP (04) dimethyl ether, but not limited thereto.

In the invention, as component (c), the good solvent, the poor solvent or a combination of those good solvent and poor solvent may be used in any form of one or more thereof either singly or as combined. Combined use of both the good solvent and the poor solvent is preferred from the viewpoint of the stability and the feeling in use. In the case where the good solvent and the poor solvent are combined for use herein, the ratio thereof, good solvent/poor solvent is preferably from 4/1 to 1/2 (by mass), more preferably from 2/1 to 1/1 (by mass).

Comprising components (a) to (c) as combined therein, the invention has made it possible for the first time to provide a translucent or transparent cosmetic composition which is excellent in actual feelings of effectiveness in use, such as a feeling of skin penetration, a feeling of non-stickiness, and a skin-softening effect after application thereof to the skin, and in stability.

In the invention, the wording "transparent to translucent" means that, when the degree of transparency of pure water is 100 and when that of a matter through which no light passes is 0, the degree of transparency (L value) of the transparent to translucent matter falls within a range of from 40 to 100. The degree of transparency of a milk-like clouded emulsion is 15 or less. The degree of transparency can be measured according to an ordinary manner, and for example, can be measured with a spectrophotometer, etc.

The cosmetic composition of the invention exhibits an effect of excellent stability even though a nonionic surfactant is not incorporated in the low-viscosity system thereof such as lotion or the like; however, from the viewpoint of further more enhancing the stability of the cosmetic composition, a hydrophilic surfactant may be optionally incorporated therein. The hydrophilic surfactant is preferably a nonionic surfactant or an anionic surfactant having HLB of at least 10, preferably HLB of at least 12.

Exemplary hydrophilic nonionic surfactant includes POE (10 to 15 mol) 2-octyldodecyl ether, POE (10 to 50 mol) decyltetradecyl ether, POE (10 to 30 mol) behenyl ether, POE (10 to 50 mol) cetyl ether, POE (20 to 60 mol) sorbitan monooleate, POE (10 to 60 mol) sorbitan monoisostearate, POE (10 to 50 mol) phytosterol ether, POE (20 to 100) hydrogenated castor oil derivative, POE (5 to 30 mol) POP (5 to 30 mol) 2-decyltetradecyl ether, POE (10 to 50 mol) POP (2 to 30 mol) cetyl ether, POE (10 to 80 mol) glyceryl monoisostearate, POE (10 to 30 mol) glyceryl monostearate, and polyether-modified silicone. Above all, preferred are POE (30 mol) 2-octyldodecyl ether, POE (30 mol) phytosterol ether, POE (60 mol) hydrogenated castor oil derivative, POE (30 mol) behenyl ether, POE (20 mol) glyceryl monoisostearate, and POE (10 mol) methylpolysiloxane copolymer, etc. As commercial products, there are mentioned NIKKOL HCO-60, NIKKOL BPS-30, NIKKOL BB-30 (all by Nikko Chemicals Co., Ltd.), EMALEX GWIS-120 (by Nihon Emulsion Co., Ltd.), KF-6017 (by Shin-Etsu Chemical Co., Ltd.), etc.

Exemplary hydrophilic anionic surfactant includes POE alkyl ether phosphate, POE/POP alkyl ether phosphate, POE sterol ether phosphate, POE/POP sterol ether phosphate, POE alkyl ether acetate, and POE/POP alkyl ether acetate. Above all, preferred is POE alkyl ether phosphate from the viewpoint of the transparency and the stability in time of the cosmetic composition. As commercial products, there are mentioned NIKKOL TDP-10, NIKKOL DDP-8, NIKKOL TCP-5 (all by Nikko Chemicals Co., Ltd.), and CRODAFOS N10A (by Croda Japan KK).

When the hydrophilic surfactant is incorporated, its ratio is preferably at most about 1/4 (ratio by mass) to component (a), more preferably at most 1/10 (ratio by mass). When the amount of the surfactant is too much, then the actual feelings of effectiveness in use of the cosmetic composition may worsen.

If desired and in addition to the above-mentioned components, any other ingredients generally incorporated in cosmetic compositions as a base may be suitably incorporated in the cosmetic composition of the invention, within a range not detracting from the advantageous effects of the invention. The optional ingredients include oils (e.g., hydrocarbon oil, synthetic ester oil, silicone oil, liquid oil and fat, solid oil and fat, and wax), powdery matters, water-soluble polymers (natural, semisynthetic, and synthetic ones), thickeners, UV absorbents, metal ion sequestrants, lower alcohols, sugars (e.g., monose, oligosaccharide, and polysaccharide), moisturizers, surfactants, organic amines, pH controlling agents, vitamins, antioxidants, antioxidation promoters, other incorporable ingredients (e.g., preservatives, antiphlogistics, skin whiteners, various vegetable oils, activators, blood circulation promoters, antiseborrheics, and antiinflammatory agents), but not limited thereto.

The form of the cosmetic composition of the invention is not specifically defined, so far as the preparation is applicable to skin. There are exemplified lotion, impregnating liquid to be impregnated in a sheet-like base, and beauty essence, etc.

EXAMPLES

The invention is described more concretely with reference to the following Examples, by which, however, the invention is not limited at all. Unless otherwise specifically indicated, the added amount is described all in terms of % by mass.

[Transparency (L Value)]

Using a spectrophotometer (by Sakata Inx Engineering Corp.), the L value of the sample was measured at room temperature. The degree of transparency of distilled water as a control was taken as 100, and those of which the degree of transparency was within a range of from 40 to less than 98 were evaluated as translucent, those of which the degree of transparency was within a range of from 98 to less than 99.5 were evaluated as transparent, and those of which the degree of transparency was within a range of from 99.5 to 100 were evaluated as extremely transparent.

[Temperature Stability]

Each sample was tested at different temperatures of 0° C., room temperature (RT), 37° C. and 50° C. (as kept in a thermostatic chamber for 4 weeks), and evaluated according to the following criteria.

(Evaluation Criteria)
- Θ: No change in appearance at 0° C., RT, 37° C. and 50° C.,
- o: No change in appearance at 0° C., RT and 37° C. At 50° C., some change occurred in appearance such as slight precipitation aggregation, separation, etc., but was on a level of no problem in practical use.
- oΔ: No change in appearance at 37° C. and RT. At 0° C. and 50° C., some change occurred in appearance such as slight precipitation aggregation, separation, etc., but was on a level of no problem in practical use.
- Δ: No change in appearance at RT. At 0° C., 37° C. and 50° C., some change occurred in appearance such as precipitation aggregation, separation, etc.
- x: Just after preparation thereof, the sample tended to precipitate; and after 4 weeks, the appearance thereof changed through precipitation aggregation, separation, etc. at any temperature of 0° C., RT, 37° C. and 50° C.

[Feeling of Penetration]

Expert panelists (10 persons) actually tried the samples, and organoleptically evaluated them in point of the feeling of penetration thereof into skin, according to the following evaluation criteria.

(Evaluation Criteria)
- Θ: Nine or more of 10 panelists answered that the feeling of penetration into skin was good.
- o: Seven or Eight of 10 panelists answered that the feeling of penetration into skin was good.
- oΔ: Five or six of 10 panelists answered that the feeling of penetration into skin was good.
- Δ: Three of four of 10 panelists answered that the feeling of penetration into skin was good.
- x: Two or less of 10 panelists answered that the feeling of penetration into skin was good.

[Feeling of Non-Stickiness]

Expert panelists (10 persons) actually tried the samples, and organoleptically evaluated them in point of the feeling of non-stickiness thereof on skin, according to the following evaluation criteria.

(Evaluation Criteria)
- Θ: Nine or more of 10 panelists answered that the tried sample was not sticky.
- o: Seven or eight of 10 panelists answered that the tried sample was not sticky.
- oΔ: Five or six of 10 panelists answered that the tried sample was not sticky.
- Δ: Three or four of 10 panelists answered that the tried sample was not sticky.
- x: Two or less of 10 panelists answered that the tried sample was not sticky.

[Skin-Softening Effect]

Expert panelists (10 persons) actually tried the samples, and organoleptically evaluated them in point of the skin-softening effect thereof, according to the following evaluation criteria.

(Evaluation Criteria)
- Θ: Nine or more of 10 panelists answered that the skin, after applied, became soft.
- o: Seven or eight of 10 panelists answered that the skin, after applied, became soft.
- oΔ: Five or six of 10 panelists answered that the skin, after applied, became soft.
- Δ: Three or four of 10 panelists answered that the skin, after applied, became soft.
- x: Two or less of 10 panelists answered that the skin, after applied, became soft.

Examples 1 to 15, Comparative Examples 1 to 4

Samples each comprising the components in the ratio shown in Table 1 below were prepared according to an ordinary method. The obtained samples were tested and evaluated for the transparency, the temperature stability and the actual feelings of effectiveness in use(feeling of penetration, feeling of non-stickiness, and skin-softening effect) thereof according to the above-mentioned evaluation methods. The results are shown in Table 1.

In Table 1, "Hydrogenated Soybean Phospholipid[*1]" is "NIKKOL Lecinol S-10E" (by Nikko Chemical Co., Ltd., having a PC content of from 75 to 85% by mass). In Comparative Examples 1 to 4, the samples could not be evaluated for the effects and the actual feelings thereof.

TABLE 1

| | Example | | | | | | | | | |
|---|---|---|---|---|---|---|---|---|---|---|
| Ingredients | 1 | 2 | 3 | 4 | 5 | 6 | 7 | 8 | 9 | 10 |
| Water | bal. | bal. | bal. | bal. | bal. | bal. | bal. | bal. | bal. | bal. |
| Ethanol | 5 | 5 | 5 | 5 | 5 | 5 | 5 | 5 | 5 | 5 |
| Glycerin | 5 | 5 | 5 | 5 | 5 | 5 | 5 | 5 | 6 | 2 |
| Solbitol | — | — | — | — | — | — | — | — | — | — |
| 1,3-Butylene Glycol | 5 | 5 | 5 | 5 | 5 | 5 | 5 | 5 | 3 | 8 |
| Hydrogenated Soybean Phospholipid(*1) | 0.3 | 0.3 | 0.001 | 0.01 | 0.5 | 1 | 0.3 | 0.3 | 0.3 | 0.3 |
| Isostearic Acid | 0.06 | — | 0.0002 | 0.002 | 0.1 | 0.2 | 0.003 | 0.12 | 0.06 | 0.06 |
| Stearic Acid | — | — | — | — | — | — | — | — | — | — |

TABLE 1-continued

|  | | | | | | | | | | |
|---|---|---|---|---|---|---|---|---|---|---|
| Isostearyl Alcohol | — | 0.06 | — | — | — | — | — | — | — | — |
| Behenyl Alcohol | — | — | — | — | — | — | — | — | — | — |
| Total | 100 | 100 | 100 | 100 | 100 | 100 | 100 | 100 | 100 | 100 |
| L Value | 80 | 75 | 98 | 98 | 70 | 60 | 82 | 81 | 82 | 85 |
| Temperature Stability | ⊙ | ⊙ | ⊙ | ⊙ | ⊙ | ○ | ⊙ | ⊙ | ⊙ | ⊙ |
| Feeling of Penetration | ⊙ | ⊙ | ○Δ | ○ | ⊙ | ⊙ | ⊙ | ⊙ | ⊙ | ⊙ |
| Feeling of Non-stickiness | ⊙ | ⊙ | ○Δ | ○ | ⊙ | ○ | ⊙ | ⊙ | ⊙ | ⊙ |
| Skin-Softening Effect | ⊙ | ⊙ | ○Δ | ○ | ⊙ | ⊙ | ⊙ | ⊙ | ⊙ | ⊙ |

|  | Example | | | | | Comparatove Example | | | |
|---|---|---|---|---|---|---|---|---|---|
| Ingredients | 11 | 12 | 13 | 14 | 15 | 1 | 2 | 3 | 4 |
| Water | bal. | bal. | bal. | bal. | bal. | bal. | bal. | bal. | bal. |
| Ethanol | 5 | 5 | 5 | 5 | 5 | 5 | 5 | 5 | 5 |
| Glycerin | 1.5 | 5 | — | 5 | 8 | 5 | 5 | 5 | — |
| Solbitol | — | — | — | 5 | — | — | — | — | — |
| 1,3-Butylene Glycol | 1.5 | — | 5 | — | 2 | 5 | 5 | 5 | — |
| Hydrogenated Soybean Phospholipid(*1) | 0.3 | 0.3 | 0.3 | 0.3 | 0.3 | 0.3 | 0.3 | 0.3 | 0.3 |
| Isostearic Acid | 0.06 | 0.06 | 0.06 | 0.06 | 0.06 | — | — | — | 0.06 |
| Stearic Acid | — | — | — | — | — | — | 0.06 | — | — |
| Isostearyl Alcohol | — | — | — | — | — | — | — | — | — |
| Behenyl Alcohol | — | — | — | — | — | — | — | 0.06 | — |
| Total | 100 | 100 | 100 | 100 | 100 | 100 | 100 | 100 | 100 |
| L Value | 65 | 50 | 55 | 43 | 52 | Precipitation | 10 | 5 | Separation |
| Temperature Stability | ⊙ | ○Δ | ○Δ | ○Δ | ○ | x | Δ | Δ | x |
| Feeling of Penetration | ⊙ | ○Δ | ○ | ○Δ | ○Δ | — | — | — | — |
| Feeling of Non-stickiness | ⊙ | ○ | ⊙ | ○Δ | ○Δ | — | — | — | — |
| Skin-Softening Effect | ⊙ | ○ | ○Δ | ○ | ○ | — | — | — | — |

Formulation Example 1

Lotion

| (Ingredients) | (% by mass) |
|---|---|
| Pure Water | bal. |
| Ethanol | 5 |
| Citric acid | q.s. |
| Sodium citrate | q.s. |
| Disodium EDTA | q.s. |
| Dynamite glycerin | 5 |
| 1,3-Butylene glycol | 5 |
| Hydrogenated soybean phospholipid ("COATSOME NC-61", by NOF Corporation) | 0.3 |
| Isostearic acid | 0.06 |
| Polyoxyethylene(30) phytosterol | 0.03 |
| Erythritol | 1 |
| Phenoxyethanol | q.s. |
| Tocopherol acetate | 0.05 |
| Fragrance | 0.01 |

Formulation Example 2

Lotion

| (Ingredients) | (% by mass) |
|---|---|
| Pure Water | bal. |
| Ethanol | 5 |
| Citric acid | q.s. |
| Sodium citrate | q.s. |
| Trisodium EDTA | q.s. |
| Dynamite glycerin | 5 |
| 1,3-Butylene glycol | 5 |

-continued

| (Ingredients) | (% by mass) |
|---|---|
| Hydrogenated soybean phospholipid ("COATSOME NC-21", by NOF Corporation) | 0.3 |
| Isostearic acid | 0.06 |
| Polyoxyethylene 400 | 1 |
| Phenoxyethanol | q.s. |
| Retinol palmitate | 0.05 |

Formulation Example 3

Moisturizing Beauty Essence

| (Ingredients) | (% by mass) |
|---|---|
| Pure Water | bal. |
| Ethanol | 3 |
| Citric acid | q.s. |
| Sodium citrate | q.s. |
| Trisodium EDTA | q.s. |
| Dynamite glycerin | 8 |
| 1,3-Butylene glycol | 10 |
| Hydrogenated soybean phospholipid ("NIKKOL Lecinol S-10E", by Nikko Chemical) | 0.5 |
| Isostearic acid | 0.1 |
| Polyoxyethylene 400 | 1 |
| Phenoxyethanol | q.s. |
| Carboxyvinyl polymer | 0.2 |
| Potassium hydroxide | 0.08 |

Formulation Example 4

Lotion

| (Ingredients) | (% by mass) |
| --- | --- |
| Pure Water | bal. |
| Ethanol | 5 |
| Citric acid | q.s. |
| Sodium citrate | q.s. |
| Trisodium EDTA | q.s. |
| Dynamite glycerin | 5 |
| 1,3-Butylene glycol | 5 |
| Hydrogenated soybean phospholipid ("NIKKOL Lecinol S-10E", by Nikko Chemical) | 0.3 |
| Isostearic acid | 0.06 |
| Polyoxyethylene 400 | 1 |
| Phenoxyethanol | q.s. |
| Retinol palmitate | 0.05 |

Formulation Example 5

Lotion

| (Ingredients) | (% by mass) |
| --- | --- |
| Pure Water | bal. |
| Ethanol | 5 |
| Citric acid | q.s. |
| Sodium citrate | q.s. |
| Trisodium EDTA | q.s. |
| Dynamite glycerin | 5 |
| 1,3-Butylene glycol | 5 |
| Hydrogenated soybean phospholipid ("BASIS LP-60HR" by Nisshin Oillio) | 0.3 |
| Isostearic acid | 0.03 |
| Linolic acid | 0.03 |
| Linolenic acid | 0.03 |
| Polyoxyethylene 400 | 1 |
| Phenoxyethanol | q.s. |
| Retinol acetate | 0.05 |

Formulation Example 6

Impregnant for Sheet Mask

| (Ingredients) | (% by mass) |
| --- | --- |
| Pure Water | bal. |
| Ethanol | 1 |
| Citric acid | q.s. |
| Sodium citrate | q.s. |
| Sodium hexametaphosphate | q.s. |
| Dynamite glycerin | 6 |
| Dipropylene glycol | 3 |
| 1,3-Butylene glycol | 3 |
| Hydrogenated soybean phospholipid ("NIKKOL Lecinol S-10E" by Nikko Chemical) | 0.5 |
| Isostearic acid | 0.08 |
| Polyoxyethylene(10) phytosterol | 0.05 |
| Carboxyvinyl polymer | 0.08 |
| Sodium hydroxide | 0.03 |
| Methylparaben | 0.15 |
| Phenoxyethanol | 0.2 |

INDUSTRIAL APPLICABILITY

According to the invention, there is provided a transparent to translucent cosmetic composition which is highly stable, and can impart excellent actual feelings of effectiveness in use, such as a feeling of skin penetration, a feeling of non-stickiness, and a skin-softening effect after application thereof to the skin.

The invention claimed is:

1. A transparent to translucent cosmetic composition, which is any one selected from the group consisting of a lotion, impregnating liquid to be impregnated in a sheet-like base, and beauty essence, comprising:
   (a) a hydrogenated phospholipid,
   (b) one or more selected from among branched higher fatty acids and higher alcohols,
   (c) a polyalcohol that acts as a good solvent and/or a poor solvent for component (a), and
   (d) water,
   wherein the ratio of component (a)/component (b) is from 1/0.01 to 1/0.4 (by mass), and
   component (a) comprises 60% by mass or more of phosphatidylcholine.

2. The cosmetic composition as claimed in claim 1, wherein component (b) is isostearic acid and/or isostearyl alcohol.

3. The cosmetic composition as claimed in claim 1, wherein component (c) that acts as a good solvent for component (a) is one or more selected from among 1,3-butylene glycol, dipropylene glycol, and propylene glycol.

4. The cosmetic composition as claimed in claim 1, wherein component (c) that acts as a poor solvent for component (a) is one or more selected from among glycerin, polyethylene glycol, polyoxyethylene methylglucoside, polyoxypropylene methylglucoside, sorbitol, and polyoxyethylene/polyoxypropylene dimethyl ether.

5. The cosmetic composition as claimed in claim 1, having an L value of from 40 to 100.

6. The cosmetic composition as claimed in claim 2, wherein component (c) that acts as a good solvent for component (a) is one or more selected from among 1,3-butylene glycol, dipropylene glycol, and propylene glycol.

7. The cosmetic composition as claimed in claim 2, wherein component (c) that acts as a poor solvent for component (a) is one or more selected from among glycerin, polyethylene glycol, polyoxyethylene methylglucoside, polyoxypropylene methylglucoside, sorbitol, and polyoxyethylene/polyoxypropylene dimethyl ether.

8. The cosmetic composition as claimed in claim 2, having an L value of from 40 to 100.

9. The cosmetic composition as claimed in claim 1, wherein the cosmetic composition comprises more than 10% by mass of (d) water.

10. The cosmetic composition as claimed in claim 1, wherein the cosmetic composition comprises the polyalcohol that acts as a good solvent for component (a) and the polyalcohol that acts as a poor solvent for component (a), and
    the ratio of the polyalcohol that acts as a good solvent for component (a)/the polyalcohol that acts as a poor solvent for component (a) is from 4/1 to 1/2 (by mass).

11. The cosmetic composition as claimed in claim 1, wherein the cosmetic composition comprises 0.001 to 3% by mass of component (a).

12. The cosmetic composition as claimed in claim 1, wherein the cosmetic composition comprises 0.01 to 1% by mass of component (a).

13. The cosmetic composition as claimed in claim 1, wherein the cosmetic composition comprises 0.01 to 0.5% by mass of component (a).

14. A method of reducing stickiness of a transparent to translucent cosmetic composition comprising (a) a hydrogenated phospholipid, (b) one or more selected from among branched higher fatty acids and higher alcohols, (c) a polyalcohol that acts as a good solvent and/or a poor solvent for component (a), and (d) water, the method comprising:
  combining component (a) and component (b) in the cosmetic composition at a ratio of component (a)/component (b) of from 1/0.01 to 1/0.4 (by mass).

* * * * *